(12) United States Patent
Pasco et al.

(10) Patent No.: US 7,846,452 B2
(45) Date of Patent: Dec. 7, 2010

(54) POTENT IMMUNOSTIMULATORY EXTRACTS FROM MICROALGAE

(75) Inventors: David Pasco, Oxford, MS (US); Nirmal Pugh, Oxford, MS (US)

(73) Assignee: The University of Mississippi, University, MS (US)

( * ) Notice: Subject to any disclaimer, the term of this patent is extended or adjusted under 35 U.S.C. 154(b) by 0 days.

(21) Appl. No.: 11/191,726

(22) Filed: Jul. 28, 2005

(65) Prior Publication Data
US 2006/0024328 A1 Feb. 2, 2006

(51) Int. Cl.
*A01N 65/03* (2009.01)
(52) U.S. Cl. .................................. 424/195.17
(58) Field of Classification Search ........................ None
See application file for complete search history.

(56) References Cited

U.S. PATENT DOCUMENTS 5,210,076 A * 5/1993 Berliner et al. ................ 514/21
5,910,433 A * 6/1999 Kajiwara et al. ............ 435/148

FOREIGN PATENT DOCUMENTS

WO    WO 02/12183    *  2/2002

OTHER PUBLICATIONS

1993. Vas et al. Characterization of melanins by Pyrolysis/Gas Chromatography/Mass Spectrometry. Rapid Comm. in Mass Spec. vol. 7, pp. 870-873.*
1954. Goodwin et al. Carotenoid synthesis in the alga *Haematococcus pluvialis*. Biochem J. Jul; 57(3) pp. 376-381.*
*Haematococcus Astaxanthin*: Applications for Human Health and Nutrition. Trends in Biotechnology. May 2003. vol. 21, No. 5. pp. 210-216.*

* cited by examiner

*Primary Examiner*—Christopher R Tate
*Assistant Examiner*—Melenie McCormick
(74) *Attorney, Agent, or Firm*—Hershkovitz & Associates LLC; Abraham Hershkovitz; Eugene C. Rzucidlo

(57) ABSTRACT

Immunostimulatory compounds can be extracted from microalgae or algae using various procedures. The resulting preparations exhibit extremely potent immunostimulatory activity. The extraction of these immunostimulatory agents is dependent on the solvent used and the extraction temperature. These preparations are potentially useful as a botanical or pharmaceutical preparation to improve immune function.

5 Claims, 5 Drawing Sheets

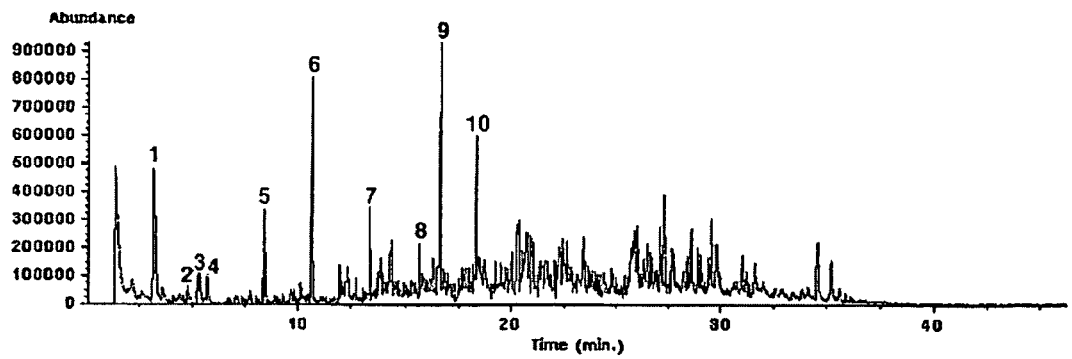
Figure 1. Total ion chromatogram of *Spirulina platensis* melanin pyrolysis products.
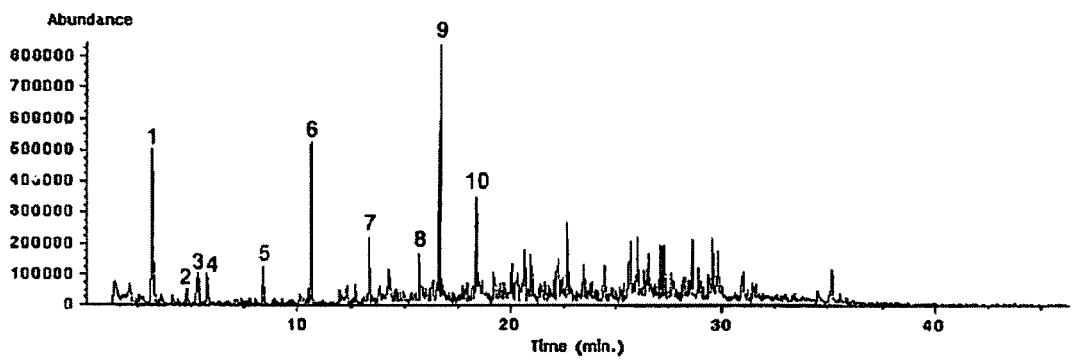
Figure 2. Total ion chromatogram of *Chlorella pyrenoidosa* melanin pyrolysis products.
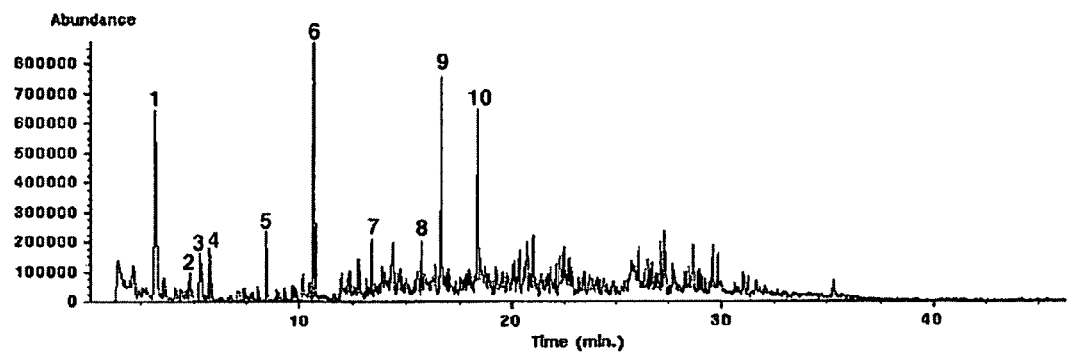
Figure 3. Total ion chromatogram of *Aphanizomenon flos-aquae* melanin pyrolysis products.

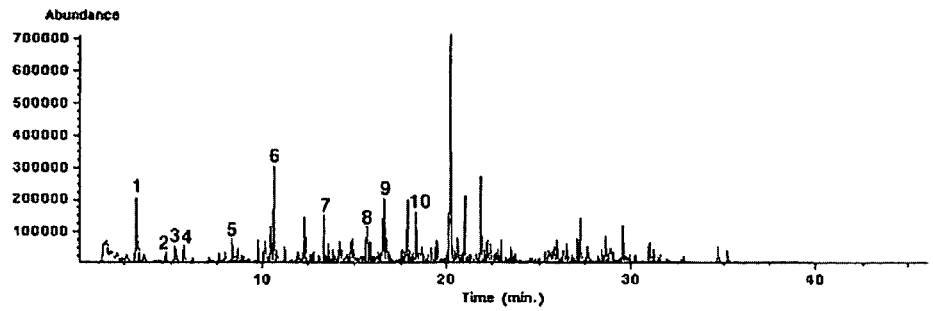

Figure 4. Total ion chromatogram of pyrolysis products for the phenol (melanin) fraction of the aqueous alcohol extract of *Spirulina platensis*.

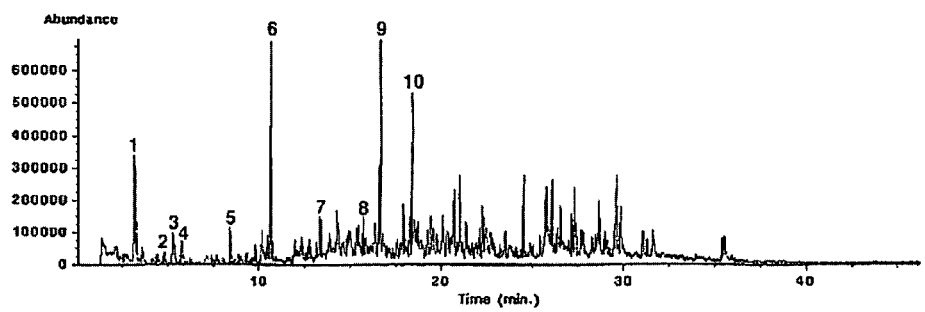

Figure 5. Total ion chromatogram of pyrolysis products for the phenol (melanin) fraction of the aqueous alcohol extract of *Chlorella pyrenoidosa*.

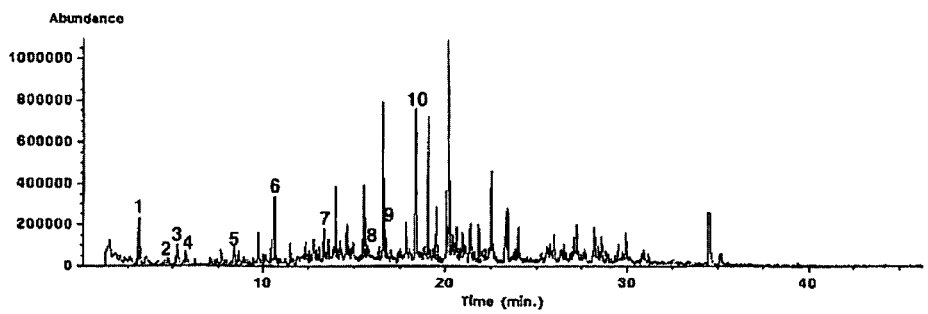

Figure 6. Total ion chromatogram of pyrolysis products for the phenol (melanin) fraction of the aqueous alcohol extract of *Aphanizomenon flos-aquae*.

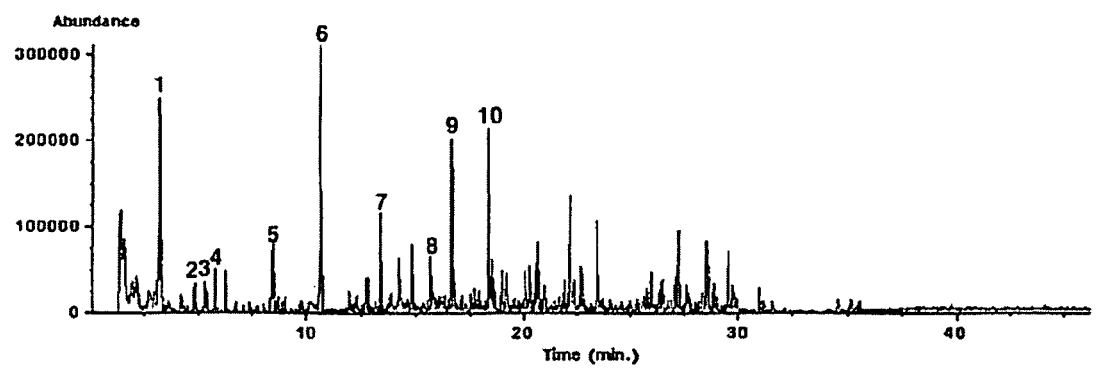
Figure 7. Total ion chromatogram of kelp (*Fucus vesiculosis*) melanin pyrolysis products.

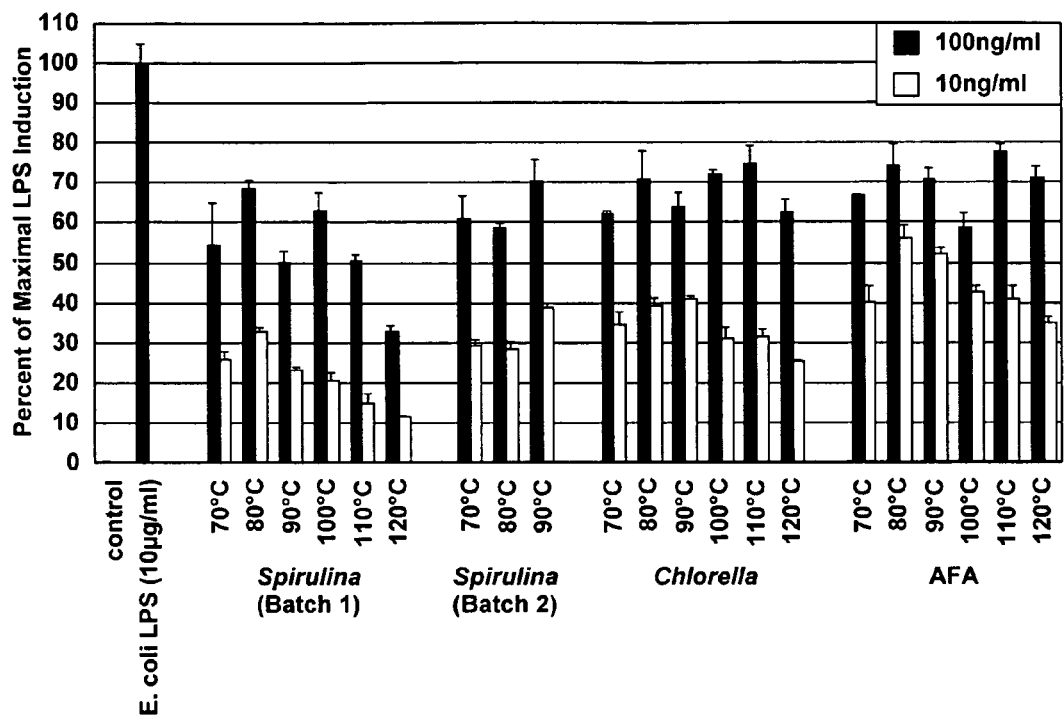
Figure 8. Activation of NF-kappa B in monocytes by crude extracts of *Spirulina platensis*, *Chlorella pyrenoidosa* and *Aphanizomenon flos-aquae* (AFA).

Fig. 9. Percent yield of crude extracts, melanin fractions and polysaccharide fractions from various extraction conditions for *Spirulina platensis*, *Chlorella pyrenoidosa* and *Aphanizomenon flos-aquae* (AFA).

| Extraction Temperature | Crude Extract Yield | Water Layer Yield (polysaccharide fraction) | Phenol Layer Yield (melanin fraction) |
|---|---|---|---|
| *Spirulina* (Batch 1) | | | |
| 70°C | 14.9% | 7.6% | 3.2% |
| 80°C | 18.6% | 10.8% | 3.5% |
| 90°C | 26.1% | 14.0% | 4.5% |
| 100°C | 28.7% | 12.1% | 6.9% |
| 110°C | 48.6% | 13.5% | 14.4% |
| 120°C | 55.4% | 9.7% | 15.4% |
| | | | |
| *Spirulina* (Batch 2) | | | |
| 70°C | 10.8% | 4.8% | 2.4% |
| 80°C | 14.8% | 6.7% | 4.0% |
| 90°C | 18.1% | 6.3% | 5.7% |
| | | | |
| *Chlorella* | | | |
| 70°C | 3.7% | 1.6% | 1.4% |
| 80°C | 5.1% | 1.9% | 2.2% |
| 90°C | 7.0% | 2.1% | 2.7% |
| 100°C | 8.3% | 2.0% | 3.4% |
| 110°C | 12.7% | 2.6% | 4.4% |
| 120°C | 16.3% | 2.1% | 7.2% |
| | | | |
| AFA | | | |
| 70°C | 8.5% | 4.7% | 2.5% |
| 80°C | 9.9% | 4.3% | 3.2% |
| 90°C | 12.3% | 3.9% | 6.1% |
| 100°C | 13.7% | 4.7% | 6.3% |
| 110°C | 19.3% | 5.3% | 10.4% |
| 120°C | 20.6% | 4.7% | 11.8% |

POTENT IMMUNOSTIMULATORY EXTRACTS FROM MICROALGAE

FIELD OF THE INVENTION

The present invention relates to the identification within algae (*Spirulina* species, *Chlorella* species, *Haematococcus pluvialis, Aphanizomenon flos-aquae* and *Fucus vesiculosis*) of high concentrations of immunostimulatory melanin. The present invention further relates to methods for the preparation of various types of extracts from the above mentioned algae. These extract preparations exhibit potent immune enhancing properties and contain substantial amounts of melanin and polysaccharides. One of these immune enhancing properties is the activation of monocytes. It also relates to methods for the treatment and/or prevention of a variety of disease conditions using the preparations of this invention.

BACKGROUND OF THE INVENTION

During the past three decades immunotherapy has become an important approach for treating human diseases and conditions through the use of regimens designed to modulate immune responses. This is particularly important in pathological conditions where the immune system becomes compromised. Studies conducted in disease models and clinical trials demonstrate that augmenting host defense mechanisms is useful in treatment and prophylaxis against microbial infections, immunodeficiencies, cancer, and autoimmune disorders (1-5). Immune enhancing protocols may also have utility for promoting wound healing. In the process of wound healing, macrophages exhibit a principal role by modulating cellular proliferation and new tissue formation/regeneration. They also function as phagocytes, debridement agents and produce growth factors that influence the angiogenesis stage of wound repair (6).

Most immunostimulants of natural origin are high molecular weight polysaccharides, glycoproteins or complex peptides (1). For example, three fungal polysaccharides derived from *Schizophyllum commune* (schizophyllan), *Lentinus edodes* (lentinan) and *Coriolus versicolor* (krestin) have been clinically used in Japan as biological response modifiers (4). Another polysaccharide, acemannan (isolated from *Aloe vera*), is licensed by the United States Department of Agriculture for the treatment of fibrosarcoma in dogs and cats (7). There are a few small molecular weight immunostimulants derived from natural products such as the glycosphingolipid KRN-7000 (8). Several immunostimulants of synthetic origin also have been developed that include compounds like isoprinosine and muramyl peptides (2). A number of other immunomodulators of endogenous origin have been developed using recombinant technologies that have gained FDA approval. These agents include colony-stimulating factors, interferons and recombinant proteins (5). However, these compounds often have short half-lives and it is difficult to determine optimal dosage and appropriate combinations.

Although current immunostimulants show promise, there is still a need to develop more potent agents and increase the arsenal of available drugs for immunotherapy. One source of chemically diverse compounds that can be used for drug discovery of immunostimulants is natural products. For centuries natural products have been exploited as therapeutically useful agents, many of which are in clinical use today. Interest in natural products as a means to drug discovery is based on their unparalleled molecular diversity and rich spectrum of biological activities (9).

Since ancient times, microalgae have been used as a nutrient-dense food source. Historical records indicate that microalgae such as *Spirulina platensis* was consumed by tribes around Lake Chad in Africa and by the Aztecs living near Lake Texcoco in Mexico (10). During the last several decades there has been increasing interest in the commercial production of food-grade microalgae for human consumption and as feed for livestock. Among the various microalgae that have been explored for their commercial potential *Spirulina* species, *Chlorella* species and *Aphanizomenon flos-aquae* (AFA) are three major types that have been successfully produced and are in widespread use. Other food-grade microalgae include *Dunaliella salina* and *Haematococcus pluvialis*.

Both anecdotal reports and recent studies on the consumption of food-grade microalgae have reported enhanced immune function in both animals and humans. Oral administration of *Chlorella vulgaris* has been correlated with enhanced natural killer cell activity (11) and granulocyte-macrophage progenitor cells (12) in mice infected with *Listeria monocytogenes*. Dietary *Spirulina platensis* increases macrophage phagocytic activity in chickens (13) and *Spirulina fusiformis* exhibits chemopreventive effects in humans (14). Human consumption of AFA has been reported to produce changes in immune cell trafficking and enhanced immune surveillance (15). The active components for all these effects have not been conclusively established.

*Chlorella* Polysaccharides and Glycoproteins

A number of polysaccharides have been identified from *Chlorella* species that possess biological activity. In U.S. Pat. No. 4,533,548 an acidic polysaccharide was isolated from *Chlorella pyrenoidosa* that exhibits antitumor and antiviral activity (16). The glycosyl composition for this polysaccharide was mostly rhamnose, with minor amounts of galactose, arabinose, glucose and glucuronic acid. Another polysaccharide, isolated from marine *Chlorella minutissima*, reported in U.S. Pat. No. 4,831,020, appears to have tumor growth-inhibiting effects. However, no molecular weight or glycosyl composition was reported (17).

In U.S. Pat. No. 4,786,496, the lipid fraction (glycolipid portion) of marine *Chlorella* species displayed antitumor properties (18). Several glycoproteins have also been isolated from *Chlorella* species. For example, U.S. Pat. No. 4,822,612 reported a 45,000 dalton glycoprotein that has anticancer effects (19). Various other glycoproteins (20-23) and glyceroglycolipids (24) that may have immunopotentiating and antitumor properties also have been reported in the scientific literature. None of these compounds are polysaccharides.

*Spirulina* Polysaccharides

Several different types of polysaccharides that exhibit biological activity have been isolated from *Spirulina* species. For example, the sulfated polysaccharide calcium spirulan inhibits tumor invasion and metastasis (25). Calcium spirulan (molecular weight 74,600 daltons) is composed of rhamnose (52.3%), 3-O-methylrhamnose (32.5%), 2,3-di-O-methylrhamnose (4.4%), 3-O-methylxylose (4.8%), uronic acids (16.5%) and sulfate (26).

U.S. Pat. No. 5,585,365 discloses that an antiviral polysaccharide with a molecular weight between 250,000 and 300,000 daltons was isolated from *Spirulina* species using hot water extraction (27). This polysaccharide is composed of rhamnose, glucose, fructose, ribose, galactose, xylose, mannose, glucuronic acid and galacturonic acid. A number of other low molecular weight polysaccharides that range between 12,600 and 60,000 daltons recently have been isolated from Spirulina species (28-30).

Previous Work by the Inventors

The present inventors have characterized novel polysaccharide preparations from the microalgae Spirulina platensis, *Chlorella pyrenoidosa* and *Aphanizomenon flos-aquae* (31). These are high molecular weight preparations that contain polysaccharides with methylated and acetylated sugars and therefore are extractable to some extent with water and also under more non polar conditions such as with aqueous alcohol.

The present inventors have also recently described a previously unrecognized class of immune stimulants and methods for their quantitative isolation from plant material (32). This class of compounds was identified as a melanin and it retains its ability to activate monocytes after isolation. It represents a major portion of the immunostimulatory activity of these botanicals.

In the present invention the inventors have applied this isolation method to quantitatively extract melanin from the following food-grade microalgae and algae: *Spirulina platensis, Chlorella pyrenoidosa, Aphanizomenon flos-aquae, Haematococcus pluvialis* and *Fucus vesiculosis* (kelp). There has not been a report of the existence of immunostimulatory melanin within these microalgae and algae.

Melanins

Melanins are complex pigment polymers that occur throughout nature. In mammalian tissue the two main types of melanin are eumelanins (black colored material that is insoluble in most solvents) and pheomelanins (yellow or reddish brown, alkali-soluble pigments). Biosynthetically, these animal melanins are derived from tyrosine oxidation by tyrosinase (coupled with thiols such as glutathione or cysteine for pheomelanins). In microorganisms, such as fungi, most melanins are derived from 1,8-dihydroxynaphthalene and contribute to virulence and modification of host immune responses (33). Although a few reports have been published on plant melanins, definitive structural data is often lacking. Some of the biological effects attributed to melanins include direct acting antiviral activity (34) and the more commonly known photoprotective/redox properties (35). The inventors have found only one report of a "melanin-like" material exhibiting immunostimulatory activity. This material was isolated from black tea leaves and when orally administered to mice, enhanced the antibody response of spleen cells to sheep red blood cells in as little as two days (36).

The insolubility of melanins in common solvents has been a major obstacle in both initial extraction as well as purification schemes. Two general isolation approaches have been developed. The first approach isolates melanin by removal of all other substances from the initial material. This elimination process typically involves harsh chemical treatments with strong acids and base. The major problems with this approach is that the melanins remain contaminated with other classes of compounds and the harsh isolation conditions leads to the destruction of native melanin structure. The second approach extracts alkali soluble melanins with either strong base at high temperatures (for example 0.5 to 3 M sodium hydroxide) or weak base (2% ammonium hydroxide) at room temperature. The immune stimulatory properties of some melanins may have been missed due to harsh treatment with base since the present inventors have found that treatment of melanin with 0.5 M sodium hydroxide completely destroys its ability to activate monocytes (32). However, the inventors have found that melanin can be qualitatively extracted using weak base and under these conditions it retains its ability to activate monocytes. Since it can be solubilized in weak base it can be subjected to chromatographic analysis. The sensitivity to strong base in addition to melanins limited solubility in commonly used solvents may explain why previous investigators did not detect this potent immunostimulatory compound in botanical material. The present inventors have developed an efficient and quantitative isolation procedure based on initial extraction with aqueous phenol that results in melanin preparations from plant material of high purity while maintaining its immunological activity (32).

Monocyte/Macrophage Activation System

One way to determine immunostimulatory activity is to use a biological assay involving macrophages. Monocytes/macrophages are found in practically every tissue of the body where they are critical in coordinating immune responses and numerous biological processes (37). They play a major role in phagocytosis, immune surveillance, wound healing, killing of microbes and tumor cells, and antigen presentation to T lymphocytes (38). In cancer, macrophages mediate tumor cytotoxicity functions through the production of cytokines and other immune factors (39). In order for macrophages to play a major role in adaptive and innate immunity they must respond effectively to environmental agents by first becoming activated (40). Macrophage activation is mediated by proinflammatory transcription factors such as nuclear factor kappa B (NF-kappa B). Such transcription factors then control and modulate the activation/repression of an array of genes that mediate a variety of immune responses.

In unstimulated macrophages, NF-kappa B exists as inactive heterodimers sequestered by inhibitory-kappa B (I-kappa B) proteins within the cytosol. Agents that cause I-kappa B proteins to dissociate and degrade allow for the translocation of NF-kappa B dimers to the nucleus where they can activate transcription of downstream genes (41). Target genes regulated by NF-kappa B include proinflammatory cytokines, chemokines, inflammatory enzymes, adhesion molecules and receptors (42).

In this invention a transcription factor based assay for NF-kappa B in human monocytes was used to guide extraction, isolation, characterization and development of immunostimulatory melanin preparations from food-grade microalgae/algae. The melanins of the present invention represent a novel class of immune stimulants.

SUMMARY OF THE INVENTION

The inventors have identified within the commonly used food-grade microalgae, such as, *Spirulina platensis, Chlorella pyrenoidosa, Haematococcus pluvialis* and *Aphanizomenon flos-aquae* high concentrations of immunostimulatory melanin. Immunostimulatory melanin was also found in *Fucus vesiculosis* (kelp). Various types of extracts from the microalgae have been prepared that contain substantial amounts of this melanin and these preparations exhibit potent immune enhancing properties. One of these properties is the activation of monocytes.

In general, the invention comprises immunostimulatory preparations isolated from food-grade microalgae and algae. According to one embodiment of the invention, immunostimulatory preparations are isolated from *Spirulina platensis* microalgae comprising melanins extractable by a solvent comprising water, weak base, phenol, or a lower alkyl alcohol or any mixture of these solvents. According to another embodiment, the immunostimulatory activity of the immunostimulatory preparation is manifested by monocyte/macrophage activation. According to another embodiment, the immunostimulatory preparation is extracted from the microalgae *Chlorella pyrenoidosa*. According to another embodiment, the immunostimulatory preparation is extracted from the microalgae *Aphanizomenon flos-aquae*. According to another embodiment, the immunostimulatory preparation is extracted from the microalgae *Haematococcus pluvialis*. According to another embodiment, the immunostimulatory preparation is extracted from the microalgae *Fucus vesiculosis* (kelp). According to another embodiment, a dietary supplement comprises any one of the previous immunostimulatory preparations and an acceptable carrier or excipient for dietary supplements.

According to another embodiment, a method of enhancing immune function in an individual in need of such treatment, comprises administering to said individual an effective amount of the microalgae-derived melanin-containing pharmaceutical composition or dietary supplement. According to another embodiment, the individual is suffering from a viral, bacterial or fungal infection. According to another embodiment, the individual is suffering from cancer. According to another embodiment, the individual is suffering from an immune deficiency. According to another embodiment, the individual is a human being. According to another embodiment, the individual is an animal.

According to another embodiment, a process to obtain a preparation from food-grade microalgae or algae enriched for immunostimulatory melanins, comprises the steps of: (a) producing an extract by extracting the microalgae with a solvent comprising water, weak base, or a mixture of water, weak base and at least one lower alkyl alcohol where the alkyl portion is from 1 to 4 carbon atoms, wherein the alcohol concentration of the mixture ranges from 0-100% by volume at an extraction temperature of between about 4 degrees C. to 120 degrees C.; (b) optionally concentrating the extract to a small volume where a large volume makes a concentration step desirable; (c) precipitating the melanin preparation out of the extract by precipitation means; (d) separating the precipitated melanin preparation by separation means; and (e) washing the precipitate of (d) with 95% alcohol. According to another embodiment, the alcohol used in the extraction process to obtain a preparation from food-grade microalgae or algae enriched for immunostimulatory melanin is ethanol. According to another embodiment, the alcohol used in the extraction process to obtain a preparation from food-grade microalgae or algae enriched for immunostimulatory melanin is methanol. According to another embodiment, the alcohol used in the extraction process to obtain a preparation from food-grade microalgae or algae enriched for immunostimulatory melanin is isopropanol or propanol. According to another embodiment, the preferred alcohol concentration in step (a) is from 20-80%. According to another embodiment, the preferred temperature of extraction is between 80 and 90 degrees C. According to another embodiment, the process is used to obtain a preparation enriched for immunostimulatory melanin from *Spirulina platensis*. According to another embodiment, the process is used to obtain a preparation enriched for immunostimulatory melanin from *Chlorella pyrenoidosa*. According to another embodiment, the process is used to obtain a preparation enriched for immunostimulatory melanin from *Aphanizomenon flos-aquae*. According to another embodiment, the process is used to obtain a preparation enriched for immunostimulatory melanin from *Haematococcus pluvialis*. According to another embodiment, the process is used to obtain a preparation enriched for immunostimulatory melanin from *Fucus vesiculosis* (kelp). According to another embodiment, the concentration step (b) is carried out (when needed) by evaporation of the solvent, preferably under reduced pressure. According to another embodiment, the concentration step (b) is carried out (when needed) by freeze drying. According to another embodiment, the concentration step (b) is carried out (when needed) by dialysis. According to another embodiment, the melanin preparation is precipitated in step (c) by the addition of ethanol to a final concentration of about 75% ethanol. According to another embodiment, the melanin preparation is precipitated in step (c) by cooling the extract. According to another embodiment, the melanin preparation is precipitated in step (c) by the addition of acid. According to another embodiment, the precipitated melanin preparation is separated in step (d) by filtration. According to another embodiment, the precipitated melanin preparation is separated in step (d) by centrifugation. According to another embodiment, the precipitated melanin preparation is washed in step (e) by 95% ethanol.

According to another embodiment, a method of treating an individual with an immunostimulatory melanin preparation in order to provide to the individual a stimulation of monocyte/macrophage activity comprises administering to the individual an effective amount of a melanin preparation extracted from food-grade microalgae or algae in combination with an acceptable carrier. According to another embodiment, the immunostimulatory melanin preparation is administered to enhance wound healing. According to another embodiment, the immunostimulatory melanin preparation is administered to treat cancer. According to another embodiment, the immunostimulatory melanin preparation is administered to treat immunodeficiency. According to another embodiment, the immunostimulatory melanin preparation is administered to treat a viral, bacterial or fungal infection. According to another embodiment, the individual is a human being. According to another embodiment, the individual is an animal. According to another embodiment, a method of treating an individual with an immunostimulatory melanin preparation in order to provide to the individual a stimulation of monocyte/macrophage activity comprises administering to the individual an effective amount of a melanin preparation extracted from *Spirulina platensis* in combination with an acceptable carrier. According to another embodiment, a method of treating an individual with an immunostimulatory melanin preparation in order to provide to the individual a stimulation of monocyte/macrophage activity comprises administering to the individual an effective amount of a melanin preparation extracted from *Chlorella pyrenoidosa*. According to another embodiment, a method of treating an individual with an immunostimulatory melanin preparation in order to provide to the individual a stimulation of monocyte/macrophage activity comprises administering to the individual an effective amount of a melanin preparation extracted from *Aphanizomenon flos-aquae*. According to another embodiment, a method of treating an individual with an immunostimulatory melanin preparation in order to provide to the individual a stimulation of monocyte/macrophage activity comprises administering to the individual an effective amount of a melanin preparation extracted from *Haematococcus pluvialis*. According to another embodiment, a method of treating an individual with an immunostimulatory melanin preparation in order to provide to the individual a stimulation of monocyte/macrophage activity comprises administering to the individual an effective amount of a melanin preparation extracted from *Fucus vesiculosis* (kelp).

BRIEF DESCRIPTION OF THE FIGURES

FIG. 1. Total ion chromatogram of *Spirulina platensis* melanin pyrolysis products. Melanin was extracted from *Spirulina platensis* using the phenol procedure. Sample was analyzed by Pyrolysis-GC-MS using a CDS Pyroprobe®

2000 at 700° C. for 10 seconds with a temperature rise of 10° C./millisecond. Compound identification was accomplished by comparison with mass spectra from the Wiley library. Peaks correspond to the following thermal decomposition products: toluene (1), ethylbenzene (2), 3-methylpyrrole (3), styrene (4), phenol (5), 4-methylphenol (6), benzene acetonitrile (7), benzene propanenitrile (8), indole (9), 7-methylindole (10).

FIG. 2. Total ion chromatogram of *Chlorella pyrenoidosa* melanin pyrolysis products. Melanin was extracted from *Chlorella pyrenoidosa* using the phenol procedure. Sample was analyzed by Pyrolysis-GC-MS using a CDS Pyroprobe® 2000 at 700° C. for 10 seconds with a temperature rise of 10° C./millisecond. Compound identification was accomplished by comparison with mass spectra from the Wiley library. Peaks correspond to the following thermal decomposition products: toluene (1), ethylbenzene (2), 3-methylpyrrole (3), styrene (4), phenol (5), 4-methylphenol (6), benzene acetonitrile (7), benzene propanenitrile (8), indole (9), 7-methylindole (10).

FIG. 3. Total ion chromatogram of *Aphanizomenon flos-aquae* melanin pyrolysis products. Melanin was extracted from *Aphanizomenon flos-aquae* using the phenol procedure. Sample was analyzed by Pyrolysis-GC-MS using a CDS Pyroprobe® 2000 at 700° C. for 10 seconds with a temperature rise of 10° C./millisecond. Compound identification was accomplished by comparison with mass spectra from the Wiley library. Peaks correspond to the following thermal decomposition products: toluene (1), ethylbenzene (2), 3-methylpyrrole (3), styrene (4), phenol (5), 4-methylphenol (6), benzene acetonitrile (7), benzene propanenitrile (8), indole (9), 7-methylindole (10).

FIG. 4. Total ion chromatogram of pyrolysis products for the phenol (melanin) fraction of the aqueous alcohol extract of *Spirulina platensis*. *Spirulina platensis* was extracted with 50% ethanol at 70° C. and this material partitioned between phenol and water. After purification the material from the phenol layer was analyzed by Pyrolysis-GC-MS using a CDS Pyroprobe® 2000 at 700° C. for 10 seconds with a temperature rise of 10° C./millisecond. Compound identification was accomplished by comparison with mass spectra from the Wiley library. Peaks correspond to the following thermal decomposition products: toluene (1), ethylbenzene (2), 3-methylpyrrole (3), styrene (4), phenol (5), 4-methylphenol (6), benzene acetonitrile (7), benzene propanenitrile (8), indole (9), 7-methylindole (10).

FIG. 5. Total ion chromatogram of pyrolysis products for the phenol (melanin) fraction of the aqueous alcohol extract of *Chlorella pyrenoidosa*. *Chlorella pyrenoidosa* was extracted with 50% ethanol at 70° C. and this material partitioned between phenol and water. After purification the material from the phenol layer was analyzed by Pyrolysis-GC-MS using a CDS Pyroprobe® 2000 at 700° C. for 10 seconds with a temperature rise of 10° C./millisecond. Compound identification was accomplished by comparison with mass spectra from the Wiley library. Peaks correspond to the following thermal decomposition products: toluene (1), ethylbenzene (2), 3-methylpyrrole (3), styrene (4), phenol (5), 4-methylphenol (6), benzene acetonitrile (7), benzene propanenitrile (8), indole (9), 7-methylindole (10).

FIG. 6. Total ion chromatogram of pyrolysis products for the phenol (melanin) fraction of the aqueous alcohol extract of *Aphanizomenon flos-aquae*. *Aphanizomenon flos-aquae* was extracted with 50% ethanol at 70° C. and this material partitioned between phenol and water. After purification the material from the phenol layer was analyzed by Pyrolysis-GC-MS using a CDS Pyroprobe® 2000 at 700° C. for 10 seconds with a temperature rise of 10° C./millisecond. Compound identification was accomplished by comparison with mass spectra from the Wiley library. Peaks correspond to the following thermal decomposition products: toluene (1), ethylbenzene (2), 3-methylpyrrole (3), styrene (4), phenol (5), 4-methylphenol (6), benzene acetonitrile (7), benzene propanenitrile (8), indole (9), 7-methylindole (10).

FIG. 7. Total ion chromatogram of kelp (*Fucus vesiculosis*) melanin pyrolysis products. Melanin was extracted from kelp using the phenol procedure. Sample was analyzed by Pyrolysis-GC-MS using a CDS Pyroprobe® 2000 at 700° C. for 10 seconds with a temperature rise of 10° C./millisecond. Compound identification was accomplished by comparison with mass spectra from the Wiley library. Peaks correspond to the following thermal decomposition products: toluene (1), ethylbenzene (2), 3-methylpyrrole (3), styrene (4), phenol (5), 4-methylphenol (6), benzene acetonitrile (7), benzene propanenitrile (8), indole (9), 7-methylindole (10).

FIG. 8. Activation of NF-kappa B in monocytes by crude extracts of *Spirulina platensis, Chlorella pyrenoidosa* and *Aphanizomenon flos-aquae* (AFA). Microalgae raw material was extracted using the aqueous alcohol extraction procedure with 50% ethanol at temperatures between 70° C. and 120° C. to produce a crude extract. Twenty-four hours following transfection with the NF-kappa B luciferase reporter plasmid, cells were treated with the crude extracts for 4 hours. Luciferase activity was determined and is reported as percent of maximal light output from LPS-treated cells. Values represent the average of duplicate determinations ± range.

FIG. 9. Percent yield of crude extracts, melanin fractions and polysaccharide fractions from various extraction conditions for *Spirulina platensis, Chlorella pyrenoidosa* and *Aphanizomenon flos-aquae* (AFA). Microalgae raw material was extracted using the aqueous alcohol extraction procedure with 50% ethanol at temperatures between 70° C. and 120° C. to produce a crude extract. To determine the content of crude melanin and crude polysaccharides, the crude extract was dissolved in water and partitioned against phenol. All yield data refers to the percent yield of the dry weight of the microalgae raw material.

DETAILED DESCRIPTION OF THE INVENTION

This invention describes the identification of immunostimulatory melanin within the following microalgae: *Spirulina platensis, Chlorella pyrenoidosa, Aphanizomenon flos-aquae* and *Haematococcus pluvialis*. In addition, immunostimulatory melanin was identified in the algae *Fucus vesiculosis*. The present invention also describes various procedures for the extraction of this material.

The extraction of melanin from Botanicals with aqueous phenol (32) or 50% ethanol between 80° C. and 90° C. (described in this invention) are the preferred methods for quantitative determination of content and activity of this material. This approach could be used for standardization of both microalgae/algae raw material and various microalgae/algae extracts. The extraction conditions using 50% ethanol at elevated temperatures, described in this invention, are suitable for production of high immunostimulatory activity preparations that contain high amounts of these immune enhancing melanins.

In addition to extracting melanin, all of the described extraction conditions also extract variable quantities of the immunostimulatory polysaccharides previously described by the inventors (31). The immunostimulatory polysaccharides that were previously identified by the inventors were isolated from *Spirulina platensis, Chlorella pyrenoidosa* and *Aphani-* zomenon flos-aquae (31). Extracts prepared from these microalgae are therefore characterized by their content/activity of both immune enhancing polysaccharides and immune enhancing melanin. Preferred conditions for the extraction of immunostimulatory polysaccharides (50% ethanol, between 40° C. and 80° C.) were previously identified by inventors (31). These conditions do not however fully extract all the immune enhancing melanin. Therefore, in the present invention improved extraction conditions (50% ethanol, between 80° C. and 90° C.) are described for production of extracts that contain optimal levels of both classes of immune stimulants.

Methods

Monocyte Assay

The transcription factor-based bioassay for activation of NF-kappa B in THP-1 human monocytes/macrophages was used to evaluate the immunostimulatory potential of melanin and polysaccharides extracted from the microalgae and algae material. This assay measures immunostimulatory activity as indicated by increased expression of a NF-kappa B-driven luciferase reporter. THP-1 human monocytes (American Type Culture Collection, Rockville, Md.) were cultured in RPMI 1640 medium supplemented with fetal bovine serum (10% v/v) and amikacin (60 mg/L) at 37° C., under 5% $CO_2$ and 95% air. Actively growing cells were transiently transfected using DEAE-dextran (10 μg/1×10$^6$ cells) and the pBI-IXLUC reporter plasmid (1 μg/1×10$^6$ cells). This plasmid, a gift from Dr. Riccardo Dalla-Favera, contains two copies of NF-kappa B motif from HIV/IgK (43). Transfection solution containing THP-1 cells was incubated for 7 minutes in a 37° C. water bath. The transfected cells were then resuspended in 10% FBS, RPMI 1640 medium and plated out in 96-well plates at a cell density of 2×10$^5$ cells per well. After 24-hours, algae extracts, fractions, and purified melanin and polysaccharide preparations were added to transfected cells. Cells were harvested and luciferase activity measured four hours after addition of samples. Cells were harvested using Silent Screen plates (HPVM membrane, Nalge Nunc International) and lysed using 40 μL of luciferase mix (1:1, luciferase assay reagent: 1×PBS, 1 mM Ca and Mg). Luciferase assay kit was purchased from Promega (Madison, Wis.). Light emission was measured using a Packard microplate scintillation counter in single photon mode. Activation is reported as a percentage relative to maximal activation of NF-kappa B by 10 μg/mL LPS (E. coli, serotype 026:B6, Sigma Chemical Co., St. Louis, Mo.) which was used as a positive control. $EC_{50}$ value for a sample represents the concentration at which light output equals 50% of those achieved by 10 μg/ml LPS.

Monoclonal antibodies to TLR2 (clone TLR2.1) and TLR4 (clone HTA125) and control antibody $IgG_{2a}$ (clone $eBM_{2a}$) were obtained from eBioscience and the monoclonal antibodies to human CD 14 (MY4) and control antibody ($MsIgG_{2b}$) were purchased from Coulter.

Phenol Extraction Procedure for Melanin

The present inventors have recently described a method for the quantitative isolation of melanin from plant material (32). The present inventors have applied this isolation method to quantitatively extract melanin from the following microalgae/algae: Spirulina platensis, Chlorella pyrenoidosa, Aphanizomenon flos-aquae, Fucus vesiculosis and Haematococcus pluvialis. The extracted melanin was also tested in the monocyte assay described above to determine if it exhibited the ability to activate these cells. This material is extracted with 90% aqueous phenol (1 g/22 ml) for 30 minutes at 70° C. and for the second extraction 16 ml is used. Active crude melanin is precipitated from the extract by addition of 6 volumes of ether/acetone (1:5). The precipitate is washed three times with ethyl acetate and twice with isopropanol. The pellet is redissolved in 90% phenol at 70° C. and undissolved material is removed by centrifugation at 3,000 rpm for 15 minutes. The phenol layer is then partitioned against equal volumes of water. The water partition is conducted at 70° C. and repeated until the top water layer is clear. The melanin material is precipitated from the phenol layer as described above and washed extensively with isopropanol and dried under vacuum.

Aqueous Alcohol Extraction Procedure for Melanin and Polysaccharides

One g of dried microalgae was extracted at a temperature between 70° C. and 120° C. with 50% ethanol, first with 7 mLs for 45 minutes and then with 5.5 mLs for 45 minutes. (Note: since 50% ethanol boils at about 80° C., extractions conducted at higher temperature were performed in sealed reaction vials). Supernatants from both extractions were combined (10 mLs) following centrifugation. The ethanol concentration of the supernatant was adjusted to 72.5% by the addition of one volume of cold 95% ethanol. Following incubation at −20° C. for several hours, precipitates were collected by centrifugation and subsequently washed with cold 95% ethanol. The isolated material was dried under vacuum and represented a crude extract containing both immunostimulatory melanin and immunostimulatory polysaccharides.

In order to determine the content/activity of melanin and polysaccharides the crude extract was dissolved in water and partitioned against phenol. During solvent partitioning, melanin partitions into the phenol layer and polysaccharides partition into the water layer. Melanin was recovered as described above, washed extensively with isopropanol and dried under vacuum. Crude polysaccharides were recovered by freeze-drying the water layer and washing the dried material several times with isopropanol.

High molecular weight polysaccharides were isolated by subjecting the crude polysaccharide material, dissolved in water, through an ultrafiltration device with a 100,000 molecular weight cut-off (Amicon Ultra-15 from Millipore, Bedford Mass.). The retentate was washed several times and then freeze-dried.

Melanin Characterization

Structural analysis of microalgae/algae melanin using filament pyrolysis-GC-MS was based on established protocols (44, 45). Samples (0.1 mg) were analyzed by Pyrolysis-GC-MS using a CDS Pyroprobe® 2000 at 700° C. for 10 seconds with a temperature rise of 10° C./millisecond. Pyrolytic products were separated using a Hewlett Packard 5890 gas chromatograph using a HP-35 column (30 m×0.25 mm ID, film thickness 0.25 μm). The GC temperature conditions were as follows: initial temperature of 50° C. for 2 minutes; increased to 290° C. at a rate of 7° C./minute; and, the final temperature was held for 10 minutes. The gas chromatograph was coupled to a Hewlett Packard 5970B Quadrupole mass spectrometer operating under electron impact conditions (ionization energy of 70 eV). All mass spectra were recorded in the mass range between 50 and 650 AMU. Identification of pyrolytic products was accomplished by comparison with mass spectra from the Wiley library database.

EXAMPLE 1

Isolation and Identification of Immunostimulatory Melanin from *Spirulina Platensis*

FIG. 1 shows the thermal degradation products resulting from filament pyrolysis-gas chromatography-mass spectrometry of melanin extracted from *Spirulina platensis* using the phenol extraction procedure. High amounts of indole as well as indole derivatives (e.g. 7-methylindole, 3-methylpyrrole) were identified. These results are consistent with melanin pyrolysis products described by others (45,46). The melanin prepared by the phenol extraction procedure constituted 19% of the dry weight of the microalgae and at 100 ng/ml activated NF-kappa B to levels 73% of those achieved with maximal levels of LPS in the monocyte assay. The carbohydrate content of this melanin preparation was 1.1% as determined by phenol/sulfuric acid calorimetric assay (47). During the isolation procedure melanin is partitioned into phenol while polar components such as polysaccharides are partitioned into water. The water layer constitutes 11% of the *Spirulina* dry weight and contains 32% carbohydrate. The activity of this material ($EC_{50}$=100 ng/ml) is similar to that of the high molecular weight polysaccharide preparations previously isolated from *Spirulina* by the inventors (31).

EXAMPLE 2

Isolation and Identification of Immunostimulatory Melanin from *Chlorella pyrenoidosa*

FIG. 2 shows the thermal degradation products resulting from filament pyrolysis-gas chromatography-mass spectrometry of melanin extracted from *Chlorella pyrenoidosa* using the phenol extraction procedure. High amounts of indole as well as indole derivatives (e.g. 7-methylindole, 3-methylpyrrole) were identified. These results are consistent with melanin pyrolysis products described by others (45,46). The melanin prepared by the phenol extraction procedure constituted 18% of the dry weight of the microalgae and at 100 ng/ml activated NF-kappa B to levels 87% of those achieved with maximal levels of LPS in the monocyte assay. The carbohydrate content of this melanin preparation was 2.3% as determined by phenol/sulfuric acid calorimetric assay (47). During the isolation procedure melanin is partitioned into phenol while polar components such as polysaccharides are partitioned into water. The water layer constitutes 4% of the *Chlorella* dry weight and contains 48% carbohydrate. The activity of this material ($EC_{50}$=100 ng/ml) is similar to that of the high molecular weight polysaccharide preparations previously isolated from *Chlorella* by the inventors (31).

EXAMPLE 3

Isolation and Identification of Immunostimulatory Melanin from *Aphanizomenon flos-aquae*

FIG. 3 shows the thermal degradation products resulting from filament pyrolysis-gas chromatography-mass spectrometry of melanin extracted from *Aphanizomenon flos-aquae* using the phenol extraction procedure. High amounts of indole as well as indole derivatives (e.g. 7-methylindole, 3-methylpyrrole) were identified. These results are consistent with melanin pyrolysis products described by others (45,46). The melanin prepared by the phenol extraction procedure constituted 46% of the dry weight of the microalgae and at 100 ng/ml activated NF-kappa B to levels 75% of those achieved with maximal levels of LPS in the monocyte assay. The carbohydrate content of this melanin preparation was 4.4% as determined by phenol/sulfuric acid colorimetric assay (47). During the isolation procedure melanin is partitioned into phenol while polar components such as polysaccharides are partitioned into water. The water layer constitutes 20% of the *Aphanizomenon flos-aquae* dry weight and contains 27% carbohydrate. The activity of this material ($EC_{50}$=25 ng/ml) is similar to that of the high molecular weight polysaccharide preparations previously isolated from *Aphanizomenon flos-aquae* by the inventors (31).

EXAMPLE 4

Preparation of Extracts for Consumption by a Subject Containing Immunostimulatory Melanin and Immunostimulatory Polysaccharides from *Spirulina platensis* Using 50% Ethanol at 70° C.

Using the aqueous alcohol extraction procedure with 50% ethanol at 70° C. an extract was prepared from *Spirulina platensis*. This extract is 10-20% of the dry weight of the microalgae and is a potent activator of monocytes as determined by the monocyte assay and represents material suitable for consumption by a subject. To determine the content/activity of melanin and polysaccharides in this extract it is dissolved in water and partitioned against phenol as described in the methods section. The melanin constituted 35% of the dry weight of this aqueous alcohol extract and exhibited an activity ($EC_{50}$=100 ng/ml) similar to the melanin extracted by the phenol procedure described in Example 1. The high molecular weight polysaccharides constitute approximately 27% of the dry weight of the 50% aqueous alcohol extract and exhibited an $EC_{50}$ of 100 ng/ml. FIG. 4 confirms that the material in the phenol layer is melanin. There was no significant contamination by melanin in the purified polysaccharide preparation since there were only trace amounts of melanin thermal degradation products (data not shown). The total yield of melanin obtained by extraction with 50% ethanol at 70° C. is substantially less than the phenol procedure (3-7% vs. 19% of the microalgae dry weight, respectively) while the activity of the isolated melanin is similar. The total yield of active polysaccharide material is similar for both extraction with 50% ethanol at 70° C. and the phenol extraction procedure (~4%).

EXAMPLE 5

Preparation of Extracts for Consumption by a Subject Containing Immunostimulatory Melanin and Immunostimulatory Polysaccharides from *Chlorella pyrenoidosa* Using 50% Ethanol at 70° C.

Using the aqueous alcohol extraction procedure with 50% ethanol at 70° C. an extract was prepared from *Chlorella pyrenoidosa*. This extract is 3-8% of the dry weight of the microalgae and is a potent activator of monocytes as determined by the monocyte assay and represents material suitable for consumption by a subject. To determine the content/activity of melanin and polysaccharides in this extract it is dissolved in water and partitioned against phenol as described in the methods section. The melanin constituted 35% of the dry weight of this aqueous alcohol extract and at 25 ng/ml activated NF-kappa B to levels similar to those seen with the melanin isolated in Example 2 (83%). The high molecular weight polysaccharides constitute approximately 30% of the dry weight of the 50% aqueous alcohol extract and exhibited an $EC_{50}$ of 5 ng/ml. FIG. 5 confirms that the material in the phenol layer is melanin. There was no significant contamination by melanin in the purified polysaccharide preparation since there were only trace amounts of melanin thermal degradation products (data not shown). The total yield of melanin obtained by extraction with 50% ethanol at 70° C. is substantially less than the phenol procedure (1-3% vs. 18% of the microalgae dry weight, respectively). The activity of the melanin isolated using the phenol procedure is approximately 2 times less active than the melanin isolated using the aqueous alcohol procedure. The total yield of active polysaccharide material is similar for both extraction with 50% ethanol at 70° C. and the phenol extraction procedure (~2%).

EXAMPLE 6

Preparation of Extracts for Consumption by a Subject Containing Immunostimulatory Melanin and Immunostimulatory Polysaccharides from *Aphanizomenon Flos-Aquae* Using 50% Ethanol at 70° C.

Using the aqueous alcohol extraction procedure with 50% ethanol at 70° C. an extract was prepared from *Aphanizomenon flos-aquae*. This extract is 10-15% of the dry weight of the microalgae and is a potent activator of monocytes as determined by the monocyte assay and represents material suitable for consumption by a subject. To determine the content/activity of melanin and polysaccharides in this extract it is dissolved in water and partitioned against phenol as described in the methods section. The melanin constituted 34% of the dry weight of this aqueous alcohol extract and at 25 ng/ml activated NF-kappa B to levels similar to those seen with the melanin isolated in Example 3 (100%). The high molecular weight polysaccharides constitute approximately 21% of the dry weight of the 50% aqueous alcohol extract and exhibited an $EC_{50}$ of 5 ng/ml. FIG. 6 confirms that the material in the phenol layer is melanin. There was no significant contamination by melanin in the purified polysaccharide preparation since there were only trace amounts of melanin thermal degradation products (data not shown). The total yield of melanin using obtained by extraction with 50% ethanol at 70° C. is substantially less than the phenol procedure (3-5% vs. 46% of the microalgae dry weight, respectively). The activity of the melanin isolated using the phenol procedure is approximately 2 times less active than the melanin isolated using the aqueous alcohol procedure. The total yield of active polysaccharide material is similar for both extraction with 50% ethanol at 70° C. and the phenol extraction procedure (~4%).

EXAMPLE 7

Extraction of Immunostimulatory Melanin from Kelp (*Fucus vesiculosis*)

FIG. 7 shows the thermal degradation products resulting from filament pyrolysis-gas chromatography-mass spectrometry of melanin extracted from kelp using the phenol extraction procedure. High amounts of indole as well as indole derivatives (e.g. 7-methylindole, 3-methylpyrrole) were identified. These results are consistent with melanin pyrolysis products described by others (45,46). The melanin prepared by the phenol extraction procedure constituted 0.2% of the dry weight of the algae and at 10 μg/ml activated NF-kappa B to levels 60% of those achieved with maximal levels of LPS in the monocyte assay.

EXAMPLE 8

Isolation and Identification of Immunostimulatory Melanin from *Haematococcus pluvialis*

Cultivation of food-grade *Haematococcus pluvialis* is of commercial interest as a rich source of astaxanthin. Since extraction of astaxanthin involves the use of non-polar solvents, the spent (or waste) material leftover after extraction may contain useful polar substances such as polysaccharides and melanin. To investigate this possibility, commercial dried *Haematococcus pluvialis* spent material was extracted with 50% ethanol at 80° C. according to the aqueous alcohol extraction procedure. This crude extract represents about 3.8% of the dry weight of the spent material. This crude extract is also a potent activator of monocytes as determined by the monocyte assay ($EC_{50}$ value between 25 ng/ml and 50 ng/ml) and represents material suitable for consumption by a subject. The content/activity of melanin and polysaccharides in this crude extract was determined. The melanin constituted 38% of the dry weight of the crude extract and at 25 ng/ml activated NF-kappa B to levels 40% of those achieved with maximal levels of LPS in the monocyte assay. The carbohydrate content of this extract was less than 1% and therefore indicates that melanin was essentially responsible for all the activity.

EXAMPLE 9

Preparation of Improved Extracts for Consumption by a Subject Containing Immunostimulatory Melanin and Immunostimulatory Polysaccharides from *Spirulina platensis* Using 50% Ethanol Between 70° C. and 120° C.

The inventors previously identified preferred conditions for the extraction of immunostimulatory polysaccharides from *Spirulina* that consisted of extraction with 50% ethanol at temperatures between 40° C. and 80° C. (31). These conditions do not however fully extract all the immune enhancing melanin as demonstrated in Example 4. Therefore, extraction conditions were optimized to produce improved extracts that contain high levels of both melanin and the previously identified polysaccharides. A variety of extraction protocols were evaluated that included extraction with various concentrations of weak base (ammonium hydroxide and phosphate buffers) alone and in combination with various concentrations of aqueous ethanol. All extraction conditions tried were less effective than 50% ethanol at 70° C. However, it was discovered that using 50% ethanol and increasing the extraction temperature above 70° C. provided optimal conditions for extraction of immunostimulatory melanin (and immunostimulatory polysaccharides). Table 1 summarizes the results obtained from extraction of *Spirulina platensis* (from two different batches of raw material) using the aqueous alcohol extraction procedure with 50% ethanol at extraction temperatures between 70° C. and 120° C. To determine the content of melanin and polysaccharides in the crude extract, the crude extract was dissolved in water and partitioned against phenol as described in the methods section. FIG. 8 shows the effect of each crude extract (tested at 25 and 100 ng/ml) on NF-kappa B activation in monocytes expressed as a percentage relative to maximal activation by 10 μg/ml LPS.

The data presented in Table 1 relays yield information for both polysaccharides and melanin in addition to crude extract yield. Table 1 shows that the yield of the crude extracts (containing both melanin and polysaccharides) increases substantially with higher extraction temperatures. The immunostimulatory activity (FIG. 8) increases (or remains the same) in crude extracts obtained with extraction temperatures at 80° C. and 90° C. as compared with extracts obtained with extraction at 70° C. However, the activity of crude extracts obtained at 100° C., 110° C. and 120° C. decreases as compared with the activity of extracts obtained with extraction temperatures between 70° C. and 90° C. This decrease in activity of crude extracts with extraction temperatures at 100° C. and above is due to enhanced extraction of a substantial amount of inactive material. This increased extraction of inactive material is reflected in the very high yields (especially at extraction temperatures with 110° C. and 120° C.). Another problem with extraction temperatures at 100° C. and above is that when these extracts cool the extract "gels" making it difficult to process.

Table 1 also shows the effect that higher extraction temperatures have on the content (yield) of melanin and polysaccharides in the crude extracts. Melanin content increases with higher extraction temperatures but polysaccharide content does not change. The enhanced yield of melanin with extraction temperatures at 100° C. and above is due to increased contaminating inactive material (as discussed above). In order to evaluate whether extraction conditions with 50% ethanol at temperatures between 70° C. and 90° C. fully extract immunostimulatory melanin, the remaining marc (spent) material from these extraction conditions was re-extracted using the phenol extraction procedure. The yield of the material obtained by extraction of the marc material was 15.5% of the dry weight of *Spirulina* but was essentially inactive when tested in the monocyte activation assay. This means that extraction conditions with 50% ethanol at temperatures between 70° C. and 90° C. are able to selectively extract most of the immunostimulatory melanin. The combined yield of melanin obtained by extraction with 50% ethanol at temperatures between 80° C. and 90° C. (3.5%-5.7%, refer to Table 1) and the material obtained by extraction of the marc material (15.5%) is approximately the same yield of melanin obtained in Example 1 (19%). This indicates that a large amount of the melanin material obtained using the phenol extraction procedure (Example 1) is contaminated with inactive material such as proteins.

The new preferred conditions for optimal extraction of both immunostimulatory melanin and immunostimulatory polysaccharides is with 50% ethanol at temperatures between 80° C. and 90° C. The increase in extraction temperature offers an improvement over existing conditions previously identified by the present inventors (31). The extracts obtained by this new process exhibit potent activation of monocytes and represents material that is suitable for consumption by a subject.

EXAMPLE 10

Preparation of Improved Extracts for Consumption by a Subject Containing Immunostimulatory Melanin and Immunostimulatory Polysaccharides from *Chlorella pyrenoidosa* Using 50% Ethanol Between 70° C. and 120° C.

The inventors previously identified preferred conditions for the extraction of immunostimulatory polysaccharides from *Chlorella* that consisted of extraction with 50% ethanol at temperatures between 40° C. and 80° C. (31). These conditions do not however fully extract all the immune enhancing melanin as demonstrated in Example 5. Therefore, extraction conditions were optimized to produce improved extracts that contain high levels of both melanin and the previously identified polysaccharides. It was discovered that using 50% ethanol and increasing the extraction temperature above 70° C. provided optimal conditions for extraction of immunostimulatory melanin (and immunostimulatory polysaccharides). Table 1 summarizes the yield results obtained from extraction of *Chlorella pyrenoidosa* using the aqueous alcohol extraction procedure with 50% ethanol at extraction temperatures between 70° C. and 120° C. To determine the content of melanin and polysaccharides in the crude extract, the crude extract was dissolved in water and partitioned against phenol as described in the methods section. FIG. 8 shows the effect of each crude extract (tested at 25 and 100 ng/ml) on NF-kappa B activation in monocytes expressed as a percentage relative to maximal activation by 10 µg/ml LPS.

From this data it is clear that the yield of the crude extracts (containing both melanin and polysaccharides) increases substantially with higher extraction temperatures. The immunostimulatory activity increases in crude extracts obtained with extraction temperatures at 80° C. and 90° C. as compared with extracts obtained with extraction at 70° C. However, the activity of crude extracts obtained at 100° C., 110° C. and 120° C. decreases as compared with the activity of extracts obtained with extraction temperatures between 70° C. and 90° C. This decrease in activity of crude extracts with extraction temperatures at 100° C. and above is due to enhanced extraction of a substantial amount of inactive material. This increased extraction of inactive material is reflected in the very high yields (especially at extraction temperatures with 110° C. and 120° C.). Another problem with extraction temperatures at 100° C. and above is that when these extracts cool there is a substantial amount of insoluble material that is inactive.

Table 1 also shows the effect that higher extraction temperatures have on the content (yield) of melanin and polysaccharides in the crude extracts. Melanin content increases with higher extraction temperatures but polysaccharide content does not change. The enhanced yield of melanin with extraction temperatures at 100° C. and above is due to increased contaminating inactive material (as discussed above).

The new preferred conditions for optimal extraction of both immunostimulatory melanin and immunostimulatory polysaccharides is with 50% ethanol at temperatures between 80° C. and 90° C. The increase in extraction temperature offers an improvement over existing conditions previously identified by the present inventors (31). The extracts obtained by this new process exhibit potent activation of monocytes and represents material that is suitable for consumption by a subject.

EXAMPLE 11

Preparation of Improved Extracts for Consumption by a Subject Containing Immunostimulatory Melanin and Immunostimulatory Polysaccharides from *Aphanizomenon flos-aquae* Using 50% Ethanol Between 70° C. and 120° C.

The inventors previously identified preferred conditions for the extraction of immunostimulatory polysaccharides from *Aphanizomenon flos-aquae* that consisted of extraction with 50% ethanol at temperatures between 40° C. and 80° C. (31). These conditions do not however fully extract all the immune enhancing melanin as demonstrated in Example 6.

Therefore, extraction conditions were optimized to produce improved extracts that contain high levels of both melanin and the previously identified polysaccharides. It was discovered that using 50% ethanol and increasing the extraction temperature above 70° C. provided optimal conditions for extraction of immunostimulatory melanin (and immunostimulatory polysaccharides). Table 1 summarizes the yield results obtained from extraction of *Aphanizomenon flos-aquae* using the aqueous alcohol extraction procedure with 50% ethanol at extraction temperatures between 70° C. and 120° C. To determine the content of melanin and polysaccharides in the crude extract, the crude extract was dissolved in water and partitioned against phenol as described in the methods section. FIG. 8 shows the effect of each crude extract (tested at 25 and 100 ng/ml) on NF-kappa B activation in monocytes expressed as a percentage relative to maximal activation by 10 μg/ml LPS.

From this data it is clear that the yield of the crude extracts (containing both melanin and polysaccharides) increases substantially with higher extraction temperatures. The immunostimulatory activity increases in crude extracts obtained with extraction temperatures at 80° C. and 90° C. as compared with extracts obtained with extraction at 70° C. However, the activity of crude extracts obtained at 100° C., 110° C. and 120° C. decreases as compared with the activity of extracts obtained with extraction temperatures between 70° C. and 90° C. This decrease in activity of crude extracts with extraction temperatures at 100° C. and above is due to enhanced extraction of a substantial amount of inactive material. This increased extraction of inactive material is reflected in the very high yields (especially at extraction temperatures with 110° C. and 120° C.). Another problem with extraction temperatures at 100° C. and above is that when these extracts cool there is a substantial amount of insoluble material that is inactive.

Table 1 also shows the effect that higher extraction temperatures have on the content (yield) of melanin and polysaccharides in the crude extracts. Melanin content increases with higher extraction temperatures but polysaccharide content does not change. The enhanced yield of melanin with extraction temperatures at 100° C. and above is due to increased contaminating inactive material (as discussed above).

The new preferred conditions for optimal extraction of both immunostimulatory melanin and immunostimulatory polysaccharides is with 50% ethanol at temperatures between 80° C. and 90° C. The increase in extraction temperature offers an improvement over existing conditions previously identified by the present inventors (31). The extracts obtained by this new process exhibit potent activation of monocytes and represents material that is suitable for consumption by a subject.

EXAMPLE 12

Activation of Monocytes by *Spirulina melanin* is not Reduced by Treatment with Proteases, Nucleases and Heating at 98° C. for 1 hour.

Extensive treatment of *Spirulina* melanin (from Example 4) with DNase 1, RNase A, proteinase K, trypsin, pronase E, nagarase or by heating at 98° C. for 1 hour did not reduce its activity in the monocyte assay, indicating that the biological activity was not due to contaminating proteins or nucleic acids (data not shown).

EXAMPLE 13

Toll-like Receptor 2 (TLR2) and CD14 are Involved in NF-kappa B Activation in Monocytes by Melanin and Polysaccharides Isolated from Microalgae The results presented in this example suggests that TLR2 and CD14 are involved in monocyte activation by melanin and high molecular weight polysaccharides isolated from *Spirulina platensis*. Treatment of cells with antibodies to TLR2 reduced NF-kappa B activation by 34% and 41% for melanin and polysaccharides, respectively. Antibodies to CD14 also suppressed activation by both agents (47% and 68% for melanin and polysaccharide, respectively) consistent with its role in mediating the action of many TLR. TLR4 antibody was ineffective at suppressing melanin-dependent and polysaccharide-dependent activation indicating the specificity of these antibodies. The control fractions for these antibodies (MsIgG2b and IgG2a) also were not effective at suppressing activation of these substances. The involvement of TLR2 and CD14 in monocyte activation by microalgae melanin is consistent with previous work by the inventors that demonstrated that both receptors were involved in monocyte activation by melanin isolated from botanicals (32).

Pharmaceutical Formulations

The present invention further includes low cost bulk melanin preparations. The microalgae from which these melanin preparations are isolated can be grown in tanks similar to current commercial methods that cultivate these microalgae for human consumption. This means that there would not be a supply problem, which is often a major issue for drug development of compounds isolated from natural products. The instant melanin preparations exist in high concentrations and can be isolated using the simple, fast and low-cost techniques of the present invention.

Since the present melanin preparations maybe useful as agents for immunotherapy in the treatment of immunodeficiency disorders, cancer, wound healing and infectious diseases, the present invention includes pharmaceutical compositions containing the instant melanin preparations optionally in combination with acceptable pharmaceutical carriers or excipients.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein. The amount of composition administered will be dependent upon the condition being treated, the subject being treated, on the subject's weight, the severity of the affliction, the manner of administration and the judgment of the personalizing physician.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the compositions compounds into preparation which can be used pharmaceutically. Proper formulation is dependent upon the route of administration chosen.

For injection, the agents of the invention may be formulated in aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, the compositions can be formulated readily by combining the active compositions with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as fit, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a power mix of the compound and a suitable powder base such as lactose or starch.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active composition may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable routes of administration may, for example, include oral, rectal, transmucosal, transdermal, or intestinal administration, parenteral delivery, including intramuscular, subcutaneous, intramedullary injections, as well as intrathecal, direct intraventricular, intravenous, intraperitoneal, intranasal, or intraocular injections.

Alternatively, one may administer the composition in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a composition of the invention formulated in a compatible pharmaceutical carrier may also be prepared, placed in an appropriate container, and labeled for treatment of an indicated condition. Suitable conditions indicated on the label may include treatment of a disease.

Dietary Supplements

Dietary supplements suitable for use in the present invention include compositions wherein the active ingredients are contained in an effective amount to achieve its intended purpose. More specifically, an effective amount means an amount effective to prevent development of or to alleviate the existing symptoms of the subject being treated. Determination of the effective amounts is well within the capability of those skilled in the art, especially in light of the detailed disclosure provided herein. The amount of composition administered will be dependent upon the condition being treated, the subject being treated, on the subjects weight, the severity of the affliction, the manner of administration and the judgment of the personalizing physician.

The ingredients of the dietary supplement of this invention are contained in acceptable excipients and/or carriers for oral consumption. The actual form of the carrier, and thus, the dietary supplement itself, may not be critical. The carrier may be a liquid, gel, gelcap, capsule, powder, solid tablet (coated or non-coated), tea or the like. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, agar, lactose, methylcellulose, povidone, carboxymethylcellulose, corn starch, and the like (including mixtures thereof). The various ingredients and the excipient and/or carrier are mixed and formed into the desired form using conventional techniques. Dose levels/unit can be adjusted to provide the recommended levels of ingredients per day in a reasonable number of units.

The dietary supplement may also contain optional ingredients including, for example, herbs, vitamins, minerals, enhancers, colorants, sweeteners, flavorants, inert ingredients, and the like. Such optional ingredients may be either naturally occurring or concentrated forms. Selection of one or several of these ingredients is a matter of formulation, design, consumer preference and end-user. The amounts of these ingredients added to the dietary supplements of this invention are readily known to the skilled artisan. Guidance to such amounts can be provided by the U.S. RDA doses for children and adults.

REFERENCES

1. Hadden, J. W. Immunostimulants. *Immunol. Today* 1993, 14, 275-280.
2. Masihi, K. N. Immunomodulatory agents for prophylaxis and therapy of infections. *Int. J. Antimicrob. Agents* 2000, 14, 181-191.
3. Van Kampen, K. R. Immunotherapy and cytokines. *Semin. Vet. Med. Surg.* (*Small Anim.*) 1997, 12, 186-192.
4. Franz, G. Polysaccharides in pharmacy: Current applications and future concepts. *Planta Med.* 1989, 55, 493-497.
5. Frank, M. O.; Mandell, G. L. Immunomodulators. *In Principles and Practice of Infectious Diseases, chapter* 33, 4th ed.; Mandell, G. L., Bennett, J. E., Dolin, R., Eds.; Churchill Livingstone: New York, 1995; pp 450-458.
6. Wilson, K. Wound healing: the role of macrophages. *Nurs. Crit. Care* 1997, 2, 291-296.
7. King, G. K.; Yates, K. M.; Greenlee, P. G.; Pierce, K. R.; Ford, C. R.; McAnalley, B. H.; Tizard, I. R. The effect of Acemannan Immunostimulant in combination with surgery and radiation therapy on spontaneous canine and feline fibrosarcomas. *J. Am. Animal Hosp. Assoc.* 1995, 31, 439-47.
8. Natori, T.; Motoki, K.; Higa, T.; Koezuka, Y. KRN7000 as a new type of antitumor and immunostimulatory drug. *In Drugs from the Sea*; Fusetani, N., Ed.; Karger: New York, 2000; pp 86-97.
9. Shu, Y. Z. Recent natural products based drug development: A pharmaceutical industry perspective. *J. Nat. Prod.* 1998, 61, 1053-1071.
10. Ciferri, O. *Spirulina*, the edible microorganism. *Microbiol. Rev.* 1983, 47, 551-578.
11. Dantas, D. C.; Kaneno, R.; Queiroz, M. L. The effects of *Chlorella vulgaris* in the protection of mice infected with *Listeria monocytogenes*. Role of natural killer cells. *Immunopharmacol. Immunotoxicol.* 1999, 21, 609-619.
12. Dantas, D. C.; Queiroz, M. L. Effects of *Chlorella vulgaris* on bone marrow progenitor cells of mice infected with *Listeria monocytogenes*. *Int. J. Immunopharmacol.* 1999, 21, 499-508.
13. Qureshi, M. A.; Garlich, J. D.; Kidd, M. T. Dietary *Spirulina platensis* enhances humoral and cell-mediated immune functions in chickens. *Immunopharmacol. Immunotoxicol.* 1996, 18, 465-476.
14. Mathew, B.; Sankaranarayanan, R.; Nair, P. P.; Varghese, C.; Somanathan, T.; Amma, B. P.; Amma, N. S.; Nair, M. K. Evaluation of chemoprevention of oral cancer with *Spirulina fusiformis*. *Nutr. Cancer* 1995, 24, 197-202.
15. Jensen, G. S.; Ginsberg, D. I.; Huerta, P.; Citton, M.; Drapeau, C. Consumption of *Aphanizomenon flos-aquae* has rapid effects on the circulation and function of immune cells in humans. JANA 2000, 2, 50-58.
16. Umezawa, I.; Komiyama, K. Acidic polysaccharide CH-1 isolated from *Chlorella pyrenoidosa* and the use thereof. U.S. Pat. No. 4,533,548, 1985.
17. Watanabe, S.; Seto, A. Ingredient effective for activating immunity obtained from *Chlorella minutissima*. U.S. Pat. No. 4,831,020, 1989.
18. Watanabe, S.; Fujita, T. Immunopotentiating agent having anti-tumor activity U.S. Pat. No. 4,786,496, 1988.
19. Shinpo, K. Anticancer agent. U.S. Pat. No. 4,822,612, 1989.
20. Noda, K.; Ohno, N.; Tanaka, K.; Okuda, M.; Yadomae, T.; Nomoto, K.; Shoyama, Y. A new type of biological response modifier from *Chlorella vulgaris* which needs protein moiety to show an antitumor activity. *Phytother Res.* 1998, 12, 309-319.
21. Tanaka, T.; Yamada, A.; Noda, K.; Hasegawa, T.; Okuda, M.; Shoyama, Y.; Nomoto, K. A novel glycoprotein obtained from *Chlorella vulgaris* strain CK22 shows antimetastatic immunopotentiation. *Cancer Immunol. Immunother.* 1998, 45, 313-320.
22. Noda, K.; Ohno, N.; Tanaka, K.; Kamiya, N.; Okuda, M.; Yadomae, T.; Nomoto, K.; Shoyama, Y. A water-soluble antitumor glycoprotein from *Chlorella vulgaris*. *Planta Med.* 1996, 62, 423-426.
23. Matsueda, S.; Shinpo, K.; Tanaka, K.; Abe, K.; Karasawa, H. Studies on anti-tumor active glycoprotein from *Chlorella vulgaris*. II. *Sci. Rep. Hirosaki Univ.* 1983, 30, 127-131.
24. Morimoto, A.; Nagatsu, A.; Murakami, N.; Sakakibara, J.; Tokuda, H.; Nishino, H.; Iwashima, A. Anti-tumor-promoting glyceroglycolipids from the green alga, *Chlorella vulgaris*. *Phytochemistry* 1995, 40, 1433-1437.

25. Mishima, T.; Murata, J.; Toyoshima, M.; Fujii, H.; Nakajima, M.; Hayashi, T.; Kato, T.; Saiki, I. Inhibition of tumor invasion and metastasis by calcium spirulan (Ca-SP), a novel sulfated polysaccharide derived from a blue-green alga, Spirulina platensis. Clin. Exp. Metastasis 1998, 16, 541-550.
26. Lee, J. B.; Hayashi, T.; Hayashi, K.; Sankawa, U.; Maeda, M.; Nemoto, T.; Nakanishi, H. Further purification and structural analysis of calcium spirulan from Spirulina platensis. J. Nat. Prod. 1998, 61, 1101-1104.
27. Hayashi, T.; Hayashi, K.; Kojima, I. Antiviral polysaccharide. U.S. Pat. No. 5,585,365, 1996.
28. Wang, H.; Zeng, H. P.; Yang, S. Z. Isolation, purification and some properties of the water-soluble polysaccharides from Spirulina platensis. Jingxi Huagong 1999, 16, 26-29.
29. Wu, J.; Zhang, C.; Liu, Y. Isolation, purification and immunological activities of extracellular polysaccharide EP II from Spirulina maxima. Yaowu Shengwu Jishu 1999, 6, 99-102.
30. Zhang, Y.; Li, H.; Gao, J.; Shen, Z.; Lin, W.; Fu, H. New process for separation and purification of polysaccharides from Spirulina platensis. Shipin Yu Fajiao Gongye 1999, 25, 15-18.
31. Pasco, D. S.; Pugh, N. D.; Ross, S. A.; ElSohly, H. N.; ElSohly, M. A. Potent immunostimulants from microalgae. PCT/US2001/21770.
32. Pasco, D. S.; Pugh, N. D.; Khan, I.; Moraes, R. Immunostimulatory Agent in Botanicals. PCT/US2004/011886.
33. Gomez, B. L.; Nosanchuk, J. D. Melanin and fungi. Curr. Opin. Infect. Dis. 2003, 16, 91-96.
34. Montefiori, D. C.; Zhou, J. Y. Selective antiviral activity of synthetic soluble L-tyrosine and L-dopa melanins against human immunodeficiency virus in vitro. Antiviral Res. 1991,15,11-25.
35. Riley, P. A. Melanin. Int. J. Biochem. Cell Biol. 1997, 29, 1235-1239.
36. Sava, V. M.; Galkin, B. N.; Hong, M. Y.; Yang, P. C.; Huang, G. S. A novel melanin-like pigment derived from black tea leaves with immuno-stimulatory activity. Food Res. Int. 2001, 34,337-343.
37. Elgert, K. D.; Alleva, D. G.; Mullins, D. W. Tumor-induced immune dysfunction: the macrophage connection. J. Leukoc. Biol. 1998, 64, 275-290.
38. Morrissette, N.; Gold, E.; Aderem, A. The macrophage: a cell for all seasons. Trends Cell. Biol. 1999, 9, 199-201.
39. Gordon, S. The role of the macrophage in immune regulation. Res. Immunol. 1998, 149, 685-688.
40. Adams, D. O.; Hamilton, T. A. Molecular basis of macrophage activation: diversity and its origins. In The Natural Immune System: The Macrophage; Lewis, C. E., McGee, J. O'D., Eds.; Oxford University Press Inc.: New York, 1992; pp 75-114.
41. May, M. J.; Ghosh, S. Signal transduction through NF-kappa B. Immunol. Today 1998, 19, 80-88.
42. Baeuerle, P. A.; Henkel, T. Function and activation of NF-kappa B in the immune system. Annu. Rev. Immunol. 1994, 12, 141-179.
43. Chang, C. C.; Zhang, J.; Lombardi, L.; Neri, A.; Dalla-Favera, R. Mechanism of expression and role in transcriptional control of the proto-oncogene NFKB-2/LYT-10. Oncogene, 1994, 9, 923-933.
44. Vas, G.; Vekey, K.; Czira, G.; Tamas, J.; Favretto, D.; Traldi, P.; Bertazzo, A.; Costa, C.; Allegri, G. Characterization of melanins by pyrolysis/gas chromatography/mass spectrometry. Rapid. Commun. Mass Spectrom. 1993, 7, 870-873.
45. Zecca, L.; Mecacci, C.; Seraglia, R.; Parati, E. The chemical characterization of melanin contained in substantia nigra of human brain. Biochim. Biophys. Acta 1992, 1138, 6-10.
46. Vekey, K.; Tamas, J.; Somogyi, A.; Bertazzo, A.; Costa, C.; Allegri, G.; Seraglia, R.; Traldi, P. Studies on structure characterization of tryptophan melanin: Comparison between filament and curie-point pyrolysis gas chromatography/mass spectrometry. Org. Mass. Spectrom. 1992, 27, 1216-1219.
47. Sturgeon, R. J. Monosaccharides: colorimetric assays. In Methods in Plant Biochemistry, vol. 2, chapter 1; Dey, P. M., Harborne, J. B., Eds.; Academic Press: New York, 1990; pp 4-12.

What is claimed:

1. An immunostimulant composition comprising a preparation obtained by extraction with a solvent comprising water, alcohol or a combination thereof, of Haematococcus pluvialis spent material wherein said spent material is the material leftover after extraction of Haematococcus pluvialis with a non-polar solvent.

2. The immunostimulant composition according to claim 1, wherein, the preparation is concentrated by precipitating the preparation.

3. An immunostimulatory agent, comprising: an immunostimulatory effective amount of the immunostimulatory composition of claims 1 or 2 and an acceptable carrier or excipient.

4. An adjuvant agent, comprising: an immunostimulatory effective amount of the immunostimulatory composition of claims 1 or 2 and an acceptable carrier or excipient.

5. A method of treating a subject requiring immune mediation comprising administering to said subject the immunostimulatory composition of claim 1.

* * * * *